(12) United States Patent
Fan et al.

(10) Patent No.: US 11,559,701 B2
(45) Date of Patent: Jan. 24, 2023

(54) METHOD AND APPARATUS TO FACILITATE ADMINISTERING THERAPEUTIC RADIATION TO A HETEROGENEOUS BODY

(71) Applicant: Varian Medical Systems International AG, Steinhausen (CH)

(72) Inventors: Zheyong Fan, Espoo (FI); Linda Laakkonen, Helsinki (FI); Ari Harju, Espoo (FI)

(73) Assignee: Varian Medical Systems International AG, Steinhausen (CH)

(*) Notice: Subject to any disclaimer, the term of this patent is extended or adjusted under 35 U.S.C. 154(b) by 31 days.

(21) Appl. No.: 17/350,212

(22) Filed: Jun. 17, 2021

(65) Prior Publication Data

US 2022/0401756 A1    Dec. 22, 2022

(51) Int. Cl.
*A61N 5/10* (2006.01)

(52) U.S. Cl.
CPC ......... *A61N 5/1031* (2013.01); *A61N 5/1075* (2013.01); *A61N 5/1077* (2013.01); *A61N 2005/1076* (2013.01)

(58) Field of Classification Search
None
See application file for complete search history.

(56) References Cited

U.S. PATENT DOCUMENTS

| | | |
|---|---|---|
| 2013/0158879 A1 | 6/2013 | Hu |
| 2014/0235923 A1 | 8/2014 | McNutt |
| 2017/0046856 A1* | 2/2017 | Hirai ................ A61B 6/00 |
| 2019/0329072 A1* | 10/2019 | Magro .............. G01T 1/161 |
| 2020/0254277 A1* | 8/2020 | Eriksson ........... G06N 3/08 |
| 2021/0016109 A1* | 1/2021 | Sjölund ............ G06N 3/084 |

OTHER PUBLICATIONS

PCT Search Report and Written Opinion from related International Application No. PCT/EP2022/065727, dated Sep. 15, 2022; 13 pages.

(Continued)

*Primary Examiner* — Hoon K Song
(74) *Attorney, Agent, or Firm* — Fitch, Even, Tabin & Flannery LLP

(57) ABSTRACT

These teachings facilitate the administration of therapeutic radiation to a heterogeneous patient volume using a radiation beam source. More particularly, these teachings provide for determining a cross-sectional size of a radiation beam as corresponds to that radiation beam source and also for determining density information corresponding to the aforementioned heterogeneous body. These teachings then provide for generating a three-dimensional radiation dose calculation for the heterogeneous body using a control circuit configured as a convolution/superposition based dose calculator using a three-dimensional energy-spreading kernel. By one approach, these teachings provide for the calculator scaling total energy released per mass as a function of the cross-sectional size and energy of the radiation beam and the aforementioned density information.

20 Claims, 3 Drawing Sheets

(56) References Cited

OTHER PUBLICATIONS

Jelen, U. et al.; A finite size pencil beam algorithm for IMRT dose optimization: density corrections; A finite size pencil beam algorithm; Physics in Medicine and Biology, Institute of Physics Publishing, Bristol, GB, vol. 52, No. 3, Feb. 7, 2007 (Feb. 7, 2007), pp. 617-633, XP020113173, ISSN: 0031-9155, DOI: 10.1088/0031-9155/52/3/006 Section 2.2.

Subhash, Sharma et al.; Dose Calculation Accuracy of the Monte Carlo Algorithm for CyberKnife Compared with other Commercially Available Dose Calculation Algorithms; Medical Dosimetry, Elsevier, US, vol. 36, No. 4, Sep. 8, 2010 (Sep. 8, 2010), pp. 347-350, XP028334364, ISSN: 0958-3947, DOI: 10.1016/J.MEDDOS. 2010.09.001 [retrieved on Sep. 16, 2010] the whole document.

* cited by examiner

METHOD AND APPARATUS TO FACILITATE ADMINISTERING THERAPEUTIC RADIATION TO A HETEROGENEOUS BODY

TECHNICAL FIELD

These teachings relate generally to treating a patient's planning target volume with radiation pursuant to a radiation treatment plan and more particularly to generating a radiation treatment plan for that patient.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Formulating a radiation treatment plan typically includes determining a dose. A Fourier transform dose calculator often serves to provide such dose information. Unfortunately, when dealing with a heterogeneous body (such as lung tissue or other bodies containing air cavities), the dose calculated by existing dose calculation methods (such as convolution/superposition based dose calculation methods including but not limited to kernel-based dose calculation methods such as Fourier transform dose calculation methods) is typically overestimated. A dose can be more accurately calculated using other approaches, but those other approaches can require considerably more time to achieve the desired calculation. By contrast, convolution/superposition based dose calculation methods are much faster and hence more desirable in a practical application setting.

BRIEF DESCRIPTION OF THE DRAWINGS

The above needs are at least partially met through provision of the method and apparatus to a therapeutic body described in the following detailed description, particularly when studied in conjunction with the drawings, wherein.

Figure 1:
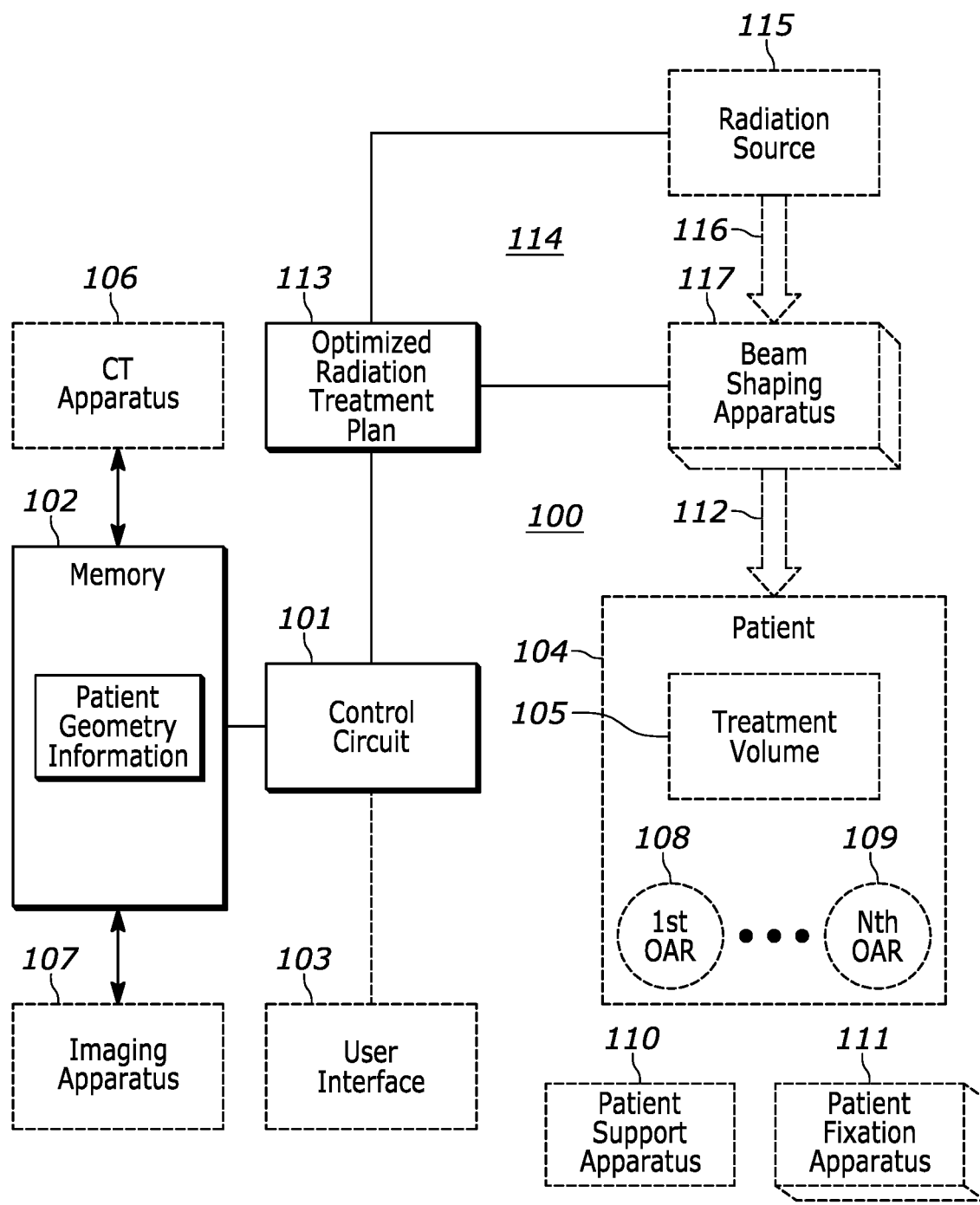
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments support the development of an optimized radiation treatment plan to effect radiation-based treatment of a patient's planning treatment volume. For the sake of an illustrative example these teachings can be carried out at least in part by an enabling control circuit. That control circuit may, or may not, be part of an integrated circuit.

These teachings provide for facilitating the administration of therapeutic radiation to a heterogeneous body, such as a heterogeneous patient volume or phantom, using a radiation beam source. More particularly, these teachings provide for determining a cross-sectional size of a radiation beam as corresponds to that radiation beam source. These teachings also provide for determining density information corresponding to the aforementioned heterogeneous body. These teachings then provide for generating a three-dimensional radiation dose calculation for the heterogeneous body using a control circuit configured as a convolution/superposition based dose calculator using a three-dimensional energy-spreading kernel. By one approach, these teachings provide for the calculator scaling total energy released per mass as a function of both the cross-sectional size of the radiation beam and the aforementioned density information.

By one approach, the calculator scales downwardly the total energy released per mass for portions of the body having a relatively lower density and scales upwardly the total energy released per mass for portions of the body having a relatively higher density. This approach can include using a scaling factor that is modeled as a function of an effective beam size, beam energy, and density at a particular point in the body.

By one approach, the aforementioned calculator can be further configured to convolve scale total energy released per mass information at a given interaction site with a primary kernel (such as a water kernel) for a reference density material.

These teachings will accommodate generating a radiation treatment plan as a function, at least in part, of the aforementioned three-dimensional radiation dose calculation and then administering therapeutic radiation to a corresponding heterogeneous patient volume per that radiation treatment plan.

In existing convolution/superposition based dose calculation methods, the total energy released per mass is calculated according to an actual density distribution, with the total energy released per mass being convolved with a water kernel to obtain the deposited dose. This approach, however, typically results in overdosing regions having a density less than water. The present teachings can provide for scaling down the total energy released per mass in lower-density regions by an appropriate factor before convolving the resultant total energy released per mass with a water kernel. In particular, these teachings can provide for modeling a corresponding scaling factor as a function of the effective beam size, beam energy, and density at a particular point in the heterogeneous body. This approach leads to more accurate results while still retaining the relatively fast computation time one ordinarily associates with convolution/superposition based dose calculation methods.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 (as when the memory 102 and control circuit 101 are both included on a shared integrated circuit) or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to optimization objectives information, patient geometry information, field geometry information, and so forth this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

In this illustrative example the control circuit 101 also operably couples to a network interface 118 that communicatively couples to one or more communication networks 119 (such as, but not limited to, the Internet). So configured the control circuit 101 can communicate with other elements (both within the apparatus 100 and external thereto, such as one or more remote entities 120) via the network interface 118. Network interfaces, including both wireless and non-wireless platforms, are well understood in the art and require no particular elaboration here.

By one approach, a computed tomography apparatus 106 and/or other non-CT imaging apparatus 107 as are known in the art can source some or all of any desired patient-related imaging information.

In this illustrative example the control circuit 101 is configured to also optionally output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various non-automated, automated, or partially-automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms. In a typical application setting the radiation treatment platform 114 will include a radiation source 115. The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
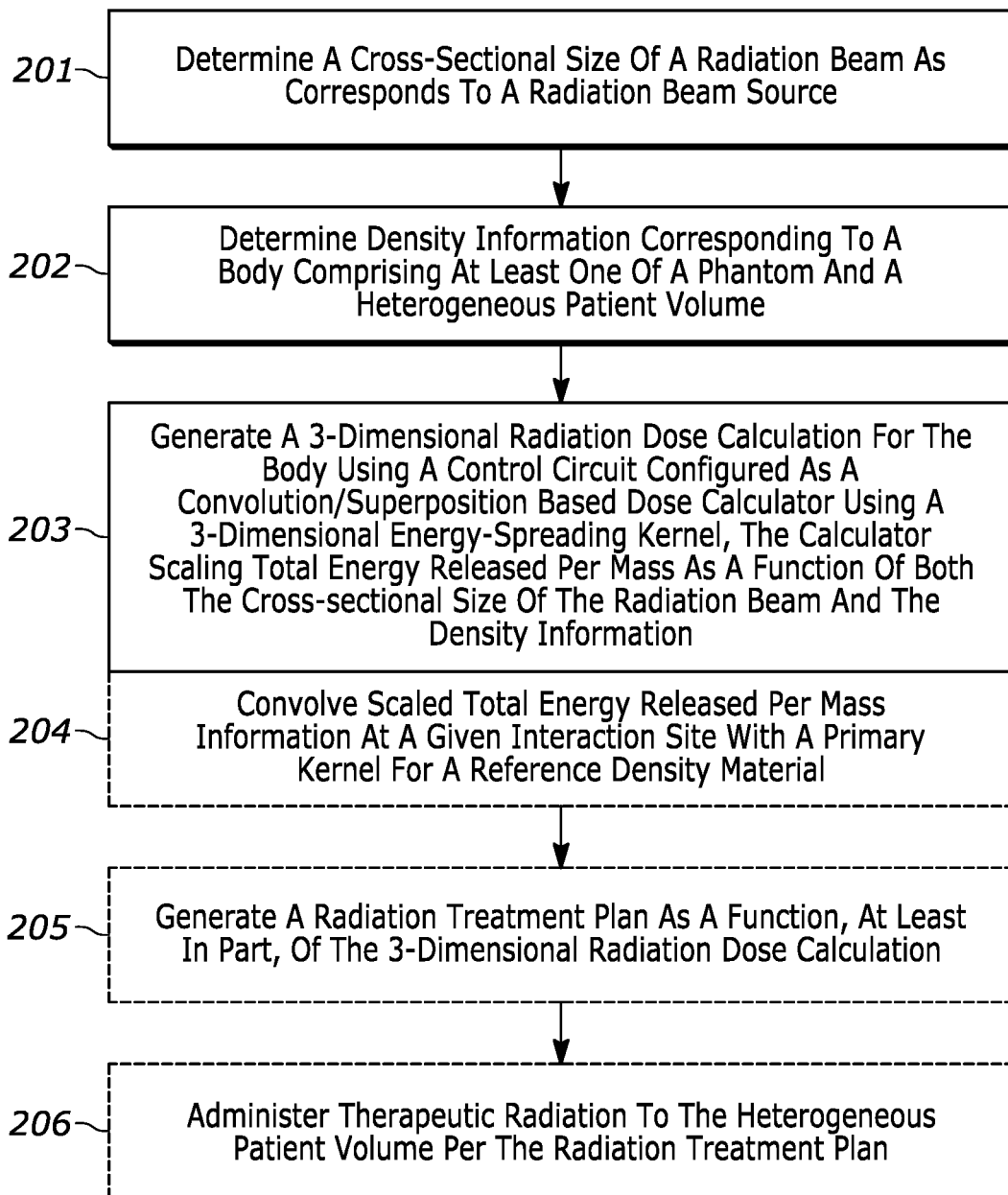
FIG. 2 comprises a flow diagram as configured in accordance with various embodiments of these teachings.

Referring now to FIG. 2, a process 200 that can be carried out, for example and at least in part, by the above-described control circuit 101 will be presented.

At block 201, this process 200 provides for determining a cross-sectional size of a radiation beam as corresponds to a radiation beam source 115. By one approach, this determination pertains to the cross-sectional size at the source. By another approach, the cross-sectional size of the beam may be referenced at a location other than at the source. Generally speaking, this cross-sectional size can be referenced and understood with respect to a Cartesian reference system. That said, this process 200 will likely provide more beneficial results when referencing an effective beam size in order to accommodate non-rectangular cross-sections (including, for example, C-shaped cross-sections).

At block 202, this process 200 provides for determining density information corresponding to a body that itself comprises at least one of a heterogeneous patient volume and a phantom. (The ordinarily-skilled person will understand that so-called phantoms are often used in clinical work for making measurements as a useful substitute for an actual measure of a volume within a patient (such as a lung). Phantoms are therefore typically comprised of a material having requisite properties, such as a similar density, to the actual patient target volume and/or a patient volume between the radiation source and the target volume itself.) It will be understood that a heterogeneous patient volume may comprise a target volume (for example, a tumor to be irradiated) or may comprise, for example, an organ at risk (including, but certainly not limited to, healthy lung tissue).

The determined density information may comprise mass density. These teachings are flexible in practice, however, and will accommodate other approaches. For example, the density information may pertain instead to such things as electron density.

At block 203, this process 200 provides for generating a three-dimensional radiation dose calculation for the heterogeneous body using, for example, the aforementioned control circuit 101 configured as a convolution/superposition based dose calculator that uses a three-dimensional energy-spreading kernel. By one approach these teachings provide for configuring this calculator to scale the total energy released per mass as a function of both the aforementioned determined cross-sectional size of the radiation beam and the aforementioned determined density information.

The aforementioned scaling may comprise, for example, scaling downwardly the total energy released per mass for portions of the body having a relatively lower density while scaling upwardly the total energy released per mass having a relatively higher density. By another approach, if desired, these teachings may provide for only scaling downwardly when necessary or scaling upwardly when necessary. The aforementioned scaling can include using a scaling factor that is modeled as a function of an effective beam size, beam energy, and density at a particular point in the aforementioned heterogeneous body.

With reference to optional block 204, these teachings will also accommodate, if desired, further configuring the aforementioned calculator to convolve scaled total energy released per mass information at a given interaction site with a primary kernel for a reference density material (such as, for example, water). So configured, these teachings permit using convolution/superposition based dose calculation methods in heterogeneous bodies in conjunction with a water kernel notwithstanding the presence of portions of the body having a density less than water.

Figure 3:
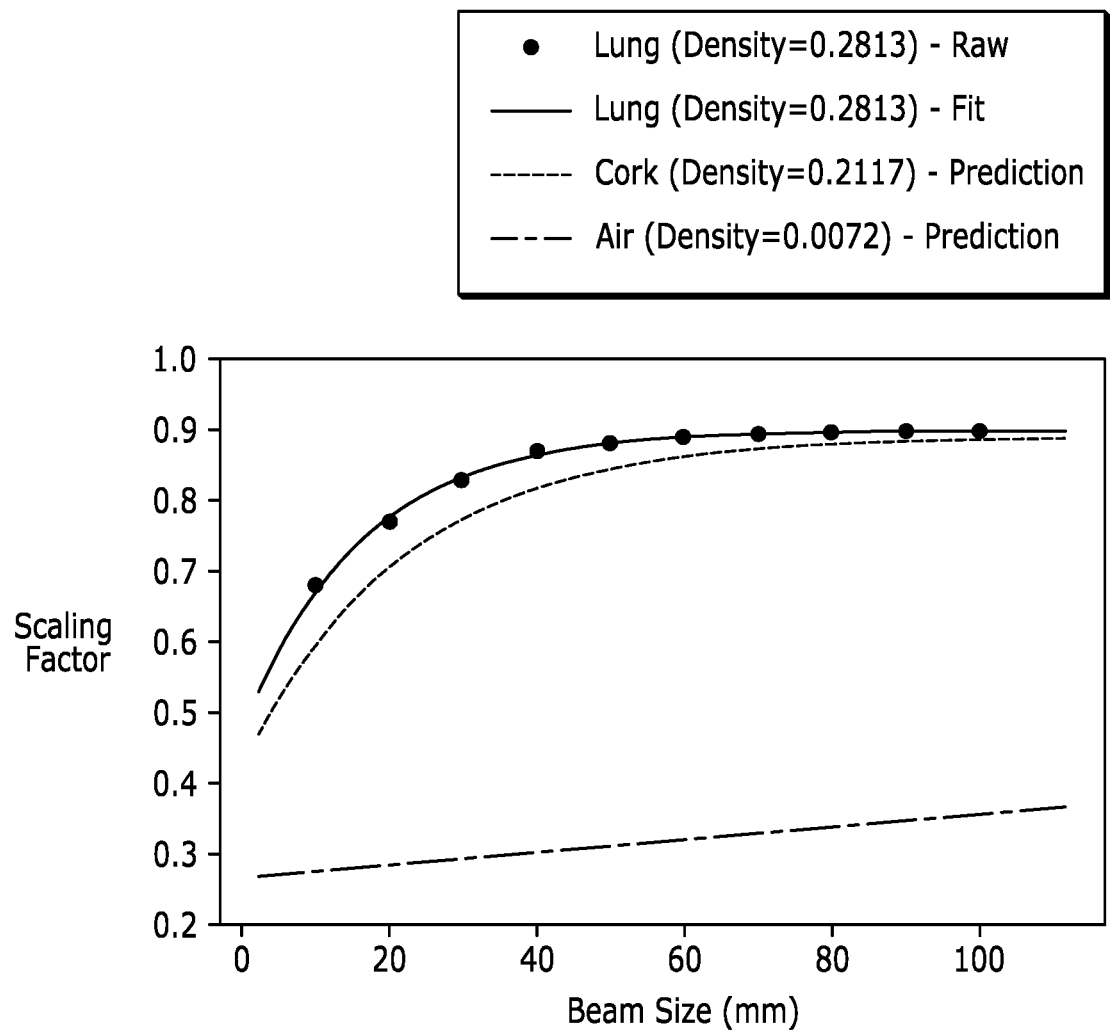
FIG. 3 comprises a graph that accords with various embodiments of these teachings.

Without intending to suggest any particular limitations as regards these teachings, the following equations offer an illustrative example as regards the foregoing. In these equations, L represents the beam size, $X_{eff}$ and $Y_{eff}$ refer to the effective width and height of the beam, ρ represents the determined density, S represents the scaling factor, r represents a Cartesian vector, and c1 through c3 are constants (where those skilled in the art will recognize that these constants represent parameters selected to match particular dose calculations; for the sake of this illustrative example, c1=0.84, c2=0.28, and c3=0.12). In this example scaling factor S is modeled as a function of the beam size and the density. The graph 300 depicted in FIG. 3 presents scaling factors for a variety of items including lung tissue, cork, and air.

$$L=\sqrt{X_{eff}Y_{eff}}$$

$$S(L,\rho(r))=1-31\ (1-\rho(r))(c_1 e^{-c_2\rho(r)L}+c_3)$$

$$T_{scaled}(r)=T(r)S(L,\rho(r))$$

The calculated result, $T_{scaled}$, constitutes the scaled total energy released per mass. That calculated value can then be utilized pursuant to ordinary prior art approaches when calculating dosing.

Although the time required to effect necessary calculations presumed by these teachings are essentially equivalent to traditional fast Fourier transform dose calculations, the applicant has determined that the accuracy achieved by these teachings is generally comparable to the anisotropic analytical algorithmic approach that ordinarily requires considerably more time than fast Fourier transform dose calculations. By retaining use of kernel uniformity (by, for example, using the water kernel), these teachings essentially leave the application of the fast Fourier transform unaffected and only introduce an additional small computational overhead (determined by the applicant to be about 10%) to accommodate the aforementioned scaling of the total energy released per mass value(s). Accordingly, those skilled in the art will recognize that these teachings are readily applicable for real-world application settings such as inverse treatment planning.

At optional block 205, this process 200 will accommodate generating a radiation treatment plan 113 as a function, at least in part, of the aforementioned three-dimensional radiation dose calculation(s). At optional block 206, this process 200 will also accommodate administering therapeutic radiation to a heterogeneous patient volume per the aforementioned radiation treatment plan 113 using, for example, the aforementioned radiation treatment platform 114.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method to facilitate the administration of therapeutic radiation to a heterogeneous patient volume using a radiation beam source, the method comprising:
   determining a cross-sectional size of a radiation beam as corresponds to the radiation beam source;
   determining density information corresponding to a body comprising at least one of a phantom and the heterogeneous patient volume;
   generating a three-dimensional radiation dose calculation for the body using a control circuit configured as a convolution/superposition based dose calculator using a three-dimensional energy-spreading kernel, wherein the calculator scales total energy released per mass as a function of both the cross-sectional size of the radiation beam and the density information.

2. The method of claim 1 wherein the heterogeneous patient volume comprises at least one of:
   a patient target volume; and
   an organ at risk.

3. The method of claim 2 wherein the patient target volume comprises, at least in part, lung tissue.

4. The method of claim 1 wherein the calculator scales downwardly the total energy released per mass for portions of the body having a relatively lower density and scales upwardly the total energy released per mass for portions of the body having a relatively higher density.

5. The method of claim 1 wherein the calculator is further configured to convolve scaled total energy released per mass information at a given interaction site with a primary kernel for a reference density material.

6. The method of claim 1 wherein the calculator is configured to scale the total energy released per mass by using a scaling factor that is modeled as a function of an effective beam size and density at a particular point in the body.

7. The method of claim 1 further comprising:
   by the control circuit:
      generating a radiation treatment plan as a function, at least in part, of the three-dimensional radiation dose calculation.

8. The method of claim 7 further comprising:
   administering therapeutic radiation to the heterogeneous patient volume per the radiation treatment plan.

9. An apparatus to facilitate the administration of therapeutic radiation to a heterogeneous patient volume using a radiation beam source, the apparatus comprising:
   a memory having stored therein:
   a cross-sectional size of a radiation beam as corresponds to the radiation beam source; and
   density information corresponding to a body comprising at least one of a phantom and the heterogeneous patient volume;
   a control circuit operably coupled to the memory and configured as a convolution/superposition based dose calculator using a three-dimensional energy-spreading kernel to generate a three-dimensional radiation dose calculation for the heterogeneous patient volume, wherein the calculator scales total energy released per mass as a function of both the cross-sectional size of the radiation beam and the density information.

10. The apparatus of claim 9 wherein the heterogeneous patient volume comprises at least one of:
    a patient target volume; and
    an organ at risk.

11. The apparatus of claim 10 wherein the patient target volume comprises, at least in part, lung tissue.

12. The apparatus of claim 9 wherein the calculator scales downwardly the total energy released per mass for portions of the body having a relatively lower density and scales upwardly the total energy released per mass for portions of the body having a relatively higher density.

13. The apparatus of claim 9 wherein the calculator is further configured to convolve scaled total energy released per mass information at a given interaction site with a primary kernel for a reference density material.

14. The apparatus of claim 9 wherein the calculator is configured to scale the total energy released per mass by using a scaling factor that is modeled as a function of an effective beam size and density at a particular point in the body.

15. The apparatus of claim 9 wherein the control circuit is further configured to:
    generate a radiation treatment plan as a function, at least in part, of the three-dimensional radiation dose calculation.

16. The apparatus of claim 15 further comprising:
    a radiation treatment platform operably coupled to the control circuit and configured to administer therapeutic radiation to the heterogeneous patient volume per the radiation treatment plan.

17. A non-transitory memory having instructions stored therein, which instructions, when executed by a control circuit, cause the control circuit to:
    determine a cross-sectional size of a radiation beam as corresponds to a radiation beam source;
    determine density information corresponding to a body comprising at least one of a phantom and a heterogeneous patient volume;
    serve as a convolution/superposition based dose calculator using a three-dimensional energy-spreading kernel to generate a three-dimensional radiation dose calculation for the heterogeneous patient volume, wherein the calculator scales total energy released per mass as a function of both the cross-sectional size of the radiation beam and the density information.

18. The non-transitory memory of claim 17 wherein the calculator is configured to scale downwardly the total energy released per mass for portions of the body having a relatively lower density and scale upwardly the total energy released per pass for portions of the body having a relatively higher density.

19. The non-transitory memory of claim 17 wherein the calculator is further configured to convolve scaled total energy released per mass information at a given interaction site with a primary kernel for a reference density material.

20. The non-transitory memory of claim 17 wherein the calculator is configured to scale the total energy released per mass by using a scaling factor that is modeled as a function of an effective beam size and density at a particular point in the body.

* * * * *